United States Patent
Yoon et al.

(10) Patent No.: US 9,567,583 B2
(45) Date of Patent: Feb. 14, 2017

(54) METHOD FOR TREATING GLIOMA USING TARBP2 EXPRESSION INHIBITOR

(71) Applicant: RESEARCH & BUSINESS FOUNDATION SUNGKYUNKWAN UNIVERSITY, Suwon-si (KR)

(72) Inventors: Keejung Yoon, Gwacheon-si (KR); Sung Hyun Byun, Suwon-si (KR)

(73) Assignee: RESEARCH & BUSINESS FOUNDATION SUNGKYUNKWAN UNIVERSITY, Suwon-si (*) Notice: Subject to any disclaimer, the term of this patent is extended or adjusted under 35 U.S.C. 154(b) by 0 days.

(21) Appl. No.: 14/558,961

(22) Filed: Dec. 3, 2014

(65) Prior Publication Data

US 2015/0111952 A1 Apr. 23, 2015

Related U.S. Application Data

(63) Continuation-in-part of application No. 14/303,665, filed on Jun. 13, 2014, now abandoned.

(30) Foreign Application Priority Data

Oct. 18, 2013 (KR) .................. 10-2013-0124943

(51) Int. Cl.
*C12N 15/11* (2006.01)
*C12N 15/113* (2010.01)

(52) U.S. Cl.
CPC .................. *C12N 15/113* (2013.01)

(58) Field of Classification Search
CPC .............. C12N 15/113; C12N 2310/141
See application file for complete search history.

(56) References Cited

U.S. PATENT DOCUMENTS

2009/0175827 A1* 7/2009 Byrom ............... A61K 31/7088
424/93.2
2009/0227533 A1* 9/2009 Bader .................. C12N 15/113
514/44 R

FOREIGN PATENT DOCUMENTS

KR 10-2006-0082928 A 7/2006

OTHER PUBLICATIONS

BLAST blastn suite-2sequences, NM_004178 vs. SEQ ID No: 1, retrieved on line on Jun. 2, 2016, pp. 1-3. http://blast.ncbi.nlm.nih.gov/Blast.cgi.*
Byun, Sung-Hyun, et al. "Upregulation of Notch Signaling Pathway by an RBP-Jk-Interacting Protein." Annual Meeting Program, 16th Annual Meeting of the Korean Society for Brain and Neural Science. Sep. 2013 (2 Pages, in English).
Korean Office Action issued on Jun. 24, 2014 in counterpart to Korean Application No. 10-2013-0124943 (5 Pages, in Korean).
Melo, Sonia A., et al. "A TARBP2 mutation in human cancer impairs microRNA processing and DICER1 function." Nature genetics vol. 41 No. 3 (2009): (8 Pages).

* cited by examiner

*Primary Examiner* — Brian Whiteman
(74) *Attorney, Agent, or Firm* — NSIP Law

(57) ABSTRACT

A method of preventing or treating glioma by inhibiting expression of Tarbp2, which is a novel transcription factor inducing Notch signal activation, and a pharmaceutical composition for treating glioma using shRNA or siRNA as a Tarbp2 expression inhibitor, as well as a method of treating glioma using the same and use thereof, are provided.

5 Claims, 7 Drawing Sheets

METHOD FOR TREATING GLIOMA USING TARBP2 EXPRESSION INHIBITOR

CROSS-REFERENCE TO RELATED APPLICATION

This application is a continuation-in-part of U.S. application Ser. No. 14/303,665, filed on Jun. 13, 2014, and claims priority to and the benefit of Korean Patent Application No. 10-2013-0124943, filed on Oct. 18, 2013, in the Korean Intellectual Property Office, the disclosure of which is incorporated herein by reference in its entirety for all purposes.

GOVERNMENT LICENSE RIGHTS

This invention was made with government support of Functional Analysis of a Novel Notch signaling pathway modulator No. 2012R1A1A2003185 grant funded by the National Research Foundation of Korea (NFR). The Government may have certain rights in the invention.

BACKGROUND

1. Field

The following description relates to a method of preventing or treating glioma by inhibiting expression of Tarbp2, which is a novel transcription factor inducing Notch signal activation, and more specifically, to a pharmaceutical composition for treating glioma using shRNA or siRNA as a Tarbp2 (Tar RNA binding protein 2) expression inhibitor, a method of treating glioma using the same and use thereof. The following description also relates to a pharmaceutical composition, which contains a novel transcription factor inducing Notch signal activation as an active component, for treating a tumor of the central nervous system such as a brain tumor or spinal tumor and to a method for treating glioma. Specifically, the following description relates to a pharmaceutical composition for treating glioma using Tar RNA binding protein 2 (Tarbp2) genes or proteins, and to a method and use of treating a brain tumor or spinal tumor such as glioma using the same.

2. Discussion of Related Art

Notch is a cell surface receptor that performs important functions during development stages by regulating cell division, apoptosis, differentiation, and the like in metazoans, and has a membrane protein structure. The term "Notch" is derived from genes that induce an excessive growth of a wing of *drosophila* in mutations and cause notches of the wing, and is a signal system for fast signal transduction and amplification between cells in multicellular organisms.

Notch sends a signal caused by cell-to-cell contact through ligands such as Delta-like 1 and Jagged attached to cells. When Notch proteins and these ligands are bound, the Notch proteins are cut by ADAM metalloprotease and γ-secretase complex. Out of the cut parts, a Notch intracellular domain (NICD) corresponding to an intracellular domain enters into a nucleus, interacts with C-promoter Binding Factor 1 (CBF1), which is a DNA binding protein, and activates or inhibits transcription of downstream genes such as Hairy/Enhancer of Split (HES). In this case, HES is one of the transcription factors that are expressed when a Notch pathway is activated as an effector of Notch signaling, and an HES family includes Hes1, Hes3, Hes5, and the like.

Research on many factors associated with Notch signaling is important for analyzing causes of various human diseases and finding treatment methods thereof. In particular, research has reported that mutations in which transcription reactions of such signaling pathways are structurally activated frequently occur in several types of cancer. Therefore, importance of pathological roles of signaling pathways such as Hedgehog and Notch is emerging.

Meanwhile, glioma is known as one of the deadly forms of cancer affecting adults. Glioma is a malignant tumor occurring in a brain or spinal cord, and occupies about 50% of primary brain tumors. About 50% of glioma patients have a very short survival time (median survival time of 12 to 16 months). Since glioma is cancer that may originate in the human brain, surgical operation is difficult, it is difficult to distinguish the glioma from normal cells, it has strong permeability and mobility, and a survival rate of patients is low. The stronger the mobility and permeability, the faster the metastasis, and tissues surrounding the cancer do not function, which causes death. Accordingly, regulation of such mobility and invasiveness will serve as an important point of a therapeutic strategy for glioma.

Gliomas are among the most devastating adult tumors for which there is currently no cure. The tumors are derived from brain glial tissue and comprise several diverse tumor forms and grades. Recent reports highlight the importance of cancer-initiating cells in the malignancy of gliomas. These cells have been referred to as brain cancer stem cells (bCSC), as they share similarities to normal neural stem cells in the brain. The Notch signaling pathway is involved in cell fate decisions throughout normal development and in stem cell proliferation and maintenance. The role of Notch in cancer is now firmly established, and recent data implicate a role for Notch signaling also in gliomas and bCSC.

Recently, demand for research on a brain tumor or spinal tumor such as glioma, and development of a therapeutic agent, has increased. However, a specific research model and method has not yet been established, and a molecular mechanism underlying these diseases has not been well-known.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The present disclosure provides a new model for treating glioma by preparing a novel transcription factor which has not yet been elucidated in a Notch signaling system, and by associating a relation between the factor and glioma for the first time.

In a general aspect, a method of treating glioma comprises administering a Tar RNA binding protein 2 (Tarbp2) expression inhibitor in a pharmaceutically effective amount to a subject.

A gene consisting of a base sequence of SEQ ID NO. 1 may encode the inhibited Tarbp2 protein.

The inhibited Tarbp2 protein may consist of an amino acid sequence of SEQ ID NO. 2.

The expression inhibitor may comprise short hairpin RNA (shRNA) or small interfering RNA (siRNA) specifically binding to Tarbp2 mRNA, or antisense RNA thereof.

The shRNA may consist of a base sequence of SEQ ID NO. 3 and the siRNA may consist of a base sequence of SEQ ID NO. 4.

The inhibited Tarbp2 may bind to C-promoter Binding Factor 1 (CBF1) protein in a Notch signaling pathway.

The inhibited Tarbp2 may increase expression of target gene Hairy and Enhancer of Split-1 (Hes1) in a Notch signaling pathway.

Other features and aspects will be apparent from the following detailed description, the drawings, and the claims.

BRIEF DESCRIPTION OF THE DRAWINGS

The above and other objects and features will become more apparent to those of ordinary skill in the art by describing in detail exemplary embodiments thereof with reference to the accompanying drawings.

Throughout the drawings and the detailed description, unless otherwise described or provided, the same drawing reference numerals or abbreviations will be understood to refer to the same elements, features, and structure.

DETAILED DESCRIPTION

Figure 1:
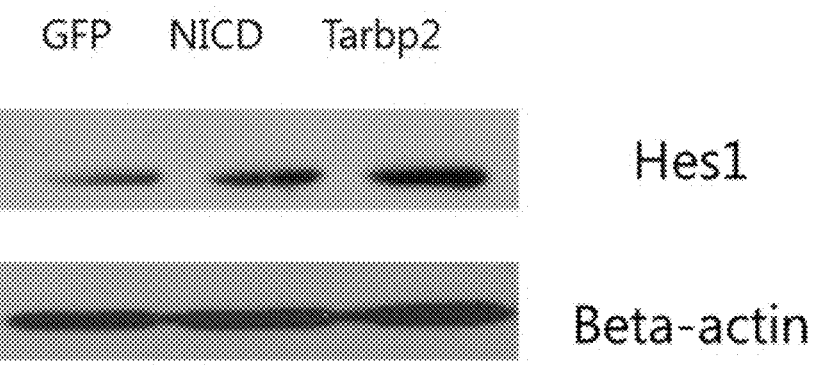
FIG. 1 is a western blot result that shows a protein expression amount of Hes1, which is a Notch target gene, when Tarbp2 is transduced in glioma cell lines. Expression of Hes1 increased, similar to a Notch intracellular domain (NICD) group in an activation state of Notch.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Notch signaling is performed by cell to cell direct contact, and is important to maintain a neural stem cell (NSC) in general. CBF1 is known as a transcription factor that plays an important role in a Notch pathway. In the present disclosure, proteins bound to CBF1 were screened through co-immunoprecipitation. Out of them, for the first time, Tar RNA binding protein 2 (Tarbp2) was identified as a novel factor that binds to CBF1.

In the related art, biological functions of TRBP have been known to affect sperm production, cell growth, cancer cell formation, and virus replication. Also, Tarbp2 has been known as a part of RNA-induced silencing complex RISC that plays an important role in miRNA processing and gene silencing. When Tarbp2 genes are transcribed, TRBP1 and TRBP2 protein isomers are expressed. The TRBP2 protein has 21 additional sequences of N-terminal amino acids compared with TRBP1. These proteins have two double strand RNA binding domains (dsRBDs) and a Medipal domain that mediates protein-protein interactions.

In addition to the functions of Tarbp2 that have been known, in the present disclosure, effects of Tarbp2 on a Notch signal and effects of Tarbp2 on differentiation and maintenance of NSC were assessed. The result showed that Tarbp2 bound to CBF1/Su(H)/Lag-1 (CSL) and served as a transcription factor, and thereby a Notch signaling pathway increased. As a result, Hes1, Hes5, Hey1, and the like, which are Notch target genes, are expressed, and it was identified that such Notch signaling activation affects a phenotype of glioma.

First, in the present disclosure, binding of Tarbp2 and CBF1 was identified using co-immunoprecipitation, and it was identified that Tarbp2 increases activation of a notch1 promoter using a luciferase reporter assay. As a result, in the present disclosure, it was identified that Tarbp2 increases expression of Hes1 and Hes5, which are Notch target genes, in the NSC.

In the present disclosure, in order to introduce Tarbp2 into glioma cells, a retrovirus vector was used. When cells are infected with the retrovirus vector, the retrovirus vector is integrated with a genetic material inside the cell and is able to make stable cell lines.

Glioma cells that have been transfected with Tarbp2 genes of the present disclosure may be prepared such that, a recombinant retrovirus vector containing nucleic acids encoding Tarbp2 is prepared, virus production cell lines are transfected with the vector to prepare recombinant virus expressing Tarbp2, and glioma cells are infected with this recombinant virus.

The virus production cell lines may use virus production cell lines corresponding to the used virus vector. For example, when the retrovirus vector is used, 293T cells, which are retrovirus production cell lines, may be used. In addition, in order to introduce the recombinant retrovirus vector expressing Tarbp2 into glioma cells, the glioma cells are plated in growth factor-containing media, treated with polybrene, and viral particles corresponding to appropriate multiplicity of infection (MOI) are added to the media to infect cells. After infection is performed, the existing virus-containing media is replaced with new glioma cell culture media and cultured.

In order to examine Notch activation characteristics of the glioma cells into which Tarbp2 is introduced according to the above method, expression of Notch target genes was examined by western blot and real time-PCR. Glioma cell lines into which Tarbp2 is introduced were lysed, and it was observed that expression of Hes1, which is a Notch target gene, increased in both protein levels and RNA levels (refer to FIGS. 1 and 2). This indicates that a Notch signaling system is activated when Tarbp2 is introduced into the glioma cell lines.

Also, in order to examine activation of Notch signal transduction when an amount of Tarbp2 is decreased in the glioma cells, a short hairpin RNA vector having a sequence complementary to Tarbp2 was prepared for transfection. When a protein amount of Hes1, which is a Notch target gene, was observed using the glioma cell lines in which Tarbp2 was knocked down, it was observed that expression of Hes1 decreased in a Tarbp2 knock down group (refer to FIG. 3).

Figure 4:
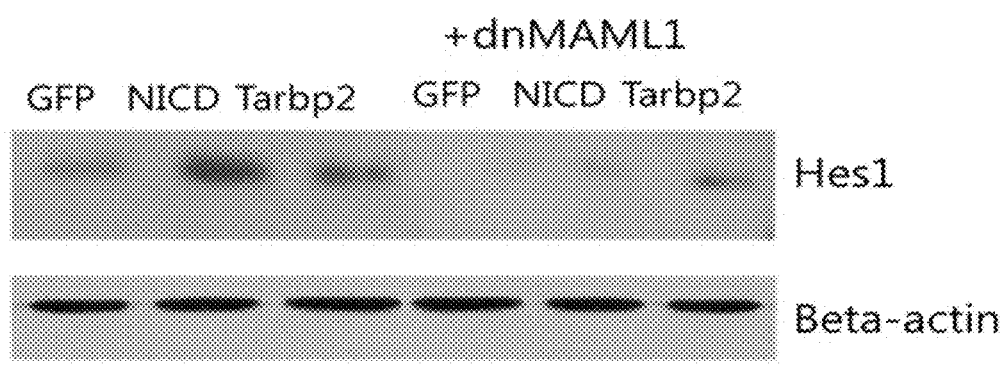
FIG. 4 is a western blot result showing that activation of a Notch signaling system is associated with Notch complex by introducing dominant negative MAML1 (dnMAML1). When Tarbp2 and dnMAML1 are transduced together, expression of Hes1 decreased.

Also, in order to examine whether this result is associated with the Notch signaling system, dominant negative MAML1 (dnMAML1) retrovirus was introduced along with Tarbp2. As a result, it was observed that a protein expression amount of Hes1 significantly decreased (refer to FIG. 4). MAML1 is an important co-activator protein for activating the Notch signaling system. When a function thereof is inhibited, expression of Hes1, which is a Notch target gene, is inhibited, which means that Tarbp2-mediated activation of Notch signaling pathway is Notch co-activator complex-dependent.

Figure 5:
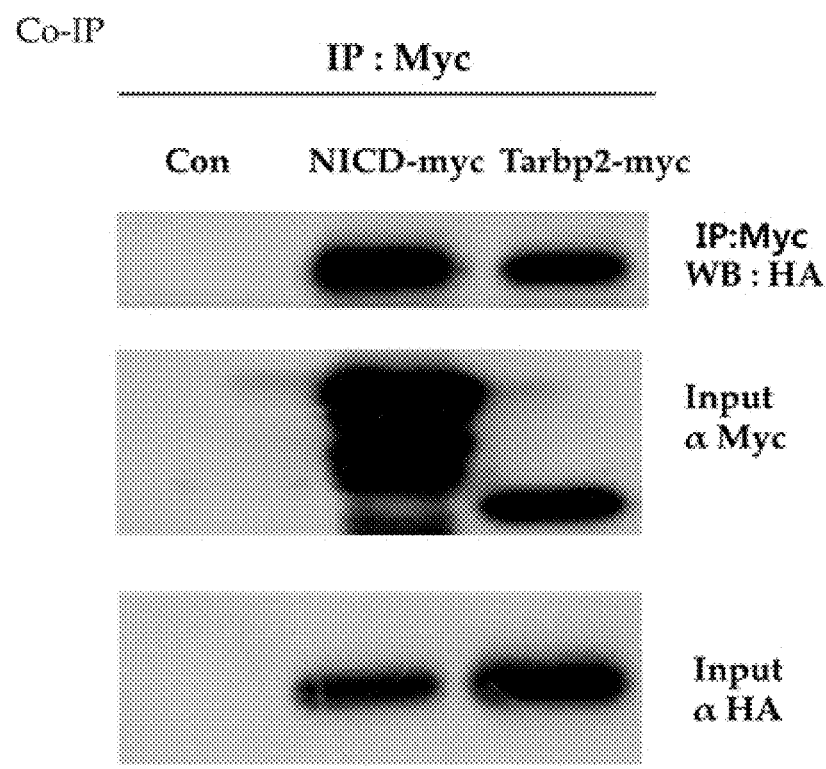
FIG. 5 is a western blot result identifying whether CBF1 and Tarbp2 are bound using a co-immunoprecipitation method. It is observed that Notch signaling activation of Tarbp2 is performed by binding it to CBF1.

Also, it was observed that Tarbp2was bound to CBF1, which is an important protein for expression of the Notch target gene, through the co-immunoprecipitation method (refer to FIG. 5). By reasoning from these results, it is identified that Tarbp2 activates the Notch signaling system by binding with CBF1 in glioma cells.

As described above, Tarbp2 of the present disclosure activates the Notch signaling system causing various types of cancer, and expression of downstream genes of Notch is inhibited when expression of Tarbp2 is inhibited. As a result, it is considered that Tarbp2 will be a new anti-cancer drug target.

Also, in order to further identify whether Tarbp2 would be a new anti-cancer drug target, it was studied whether proliferation and migration of glioma cells were inhibited when Tarbp2 expression in glioma cells was knocked down. Specifically, when shRNA specific to Tarbp2 mRNA was introduced, and cell counting and a wound-healing assay were performed, it was observed that proliferation and migration were inhibited (refer to FIGS. 6 and 7). In particular, since glioma is cancer having a strong ability to proliferate, having permeability and mobility, and is easily spread to surrounding tissues, inhibition of proliferation and migration may be used as an important strategy for treatment for glioma.

A treatment composition of the present disclosure may further include components such as an existing treatment active component, other adjuvants, and a pharmaceutically acceptable carrier. Examples of the pharmaceutically acceptable carrier include saline, sterile water, Ringer's solution, buffered saline, dextrose solution, maltodextrin solution, glycerol, and ethanol.

Also, the present disclosure provides a method of preventing or treating glioma by administering a pharmaceutical composition containing Tarbp2 expression inhibitor of a pharmaceutically effective amount to a subject.

The term "expression inhibition" used herein refers to causing a functional decrease in a target gene, and preferably, refers to the fact that detection of target gene expression becomes impossible or target gene expression remains at an insignificant level due to expression inhibition.

The term "expression inhibitor" used herein includes shRNA, siRNA, microRNA, antisense oligonucleotide, PNA, aptamer, and the like, but the claimed invention may not be limited thereto.

The term "siRNA" used herein refers to a short double-stranded RNA capable of inducing an RNA interference (RNAi) through a cleavage of a specific mRNA. siRNA includes a sense RNA strand having a sequence homologous to mRNA of the target gene, and an antisense RNA strand having a sequence complementary thereto. Since siRNA is able to inhibit expression of the target gene, it may be provided as a useful gene knock-down or a gene therapy tool.

The term "small hairpin RNA (shRNA)" used herein refers to single-stranded 50 to 60 nucleotides forming a stem-loop structure in vivo. That is, shRNA is an RNA sequence forming a tight hairpin structure for inhibiting gene expression through RNA interference. Inside of a loop region of 5 to 10 nucleotides, a long RNA of complementary 15 to 30 nucleotides makes a base pair to form a double-stranded stem. In order to express, shRNA may be transduced into cells through a vector including a U6 promoter and is usually delivered to daughter cells such that gene expression inhibition is inherited. The shRNA hairpin structure is cut by an intracellular mechanism, results in siRNA, and then binds to an RNA-induced silencing complex (RISC). These RISCs bind to mRNA and cut them. shRNA is transcribed by RNA polymerase III. In the present disclosure, the term "subject" refers to an object that requires treatment of diseases, and more specifically, refers to mammals such as human or nonhuman primates, mouse, rat, dog, cat, horse, and cattle. Also, in the present disclosure, the term "pharmaceutically effective amount" is determined by factors including types and severity of diseases, a patient's age and sex, drug sensitivity, an administration time, an administration route, a discharge rate, a treatment duration, and simultaneously used drugs, and other factors well-known in the field of medicine. The pharmaceutically effective amount is an amount that can achieve a maximum effect without side effects in consideration of all of the above factors, and may be easily determined by those skilled in the art.

A method of administering the composition of the present disclosure has no limitation as long as it can reach target tissues. For example, the method includes oral administration, arterial injection, intravenous injection, percutaneous injection, intranasal administration, intratracheal instillation, or intramuscular injection. A daily dosage is about 0.0001 to 100 mg/kg, and preferably, 0.001 to 10 mg/kg. It is preferable that the dosage be divided and administered once to several times a day.

Administering a composition comprising Tarbp2 protein may, for example, employ invasive, pharmacological, or physiological approaches. An invasive approach may include intra-cerebro-ventricular infusion, convection-enhanced delivery, intra-cerebral injection or use of implants, or disruption of the BBB. A pharmacological approach may include modification of charge, lipophilicity, relative number of polar groups, and use of lipid carriers. A physiological approach may include use of transporter-mediated delivery, receptor-mediated transcytosis, transferrin receptor, insulin receptor, and low-density lipoprotein. Use of insulin receptors may include antibodies against transferrin receptor and human insulin receptor for brain drug targeting; liposomes coated with targeting molecules such as antibodies, Trojan Horses Liposomes (THL); and nanoparticles coated with transferrin or transferrin receptor antibodies.

Administering a composition comprising Tarbp2 gene may, for example, employ gene therapy. Gene therapy may include the use of retroviruses, adenoviruses, envelope protein pseudotyping of viral vectors, replication-competent vectors, cis and trans-acting elements, or herpes simplex virus. Non-viral methods in gene therapy may also be used. Hereinafter, in order to facilitate understanding of the present disclosure, certain examples are provided. However, the following examples are provided to easily understand the present disclosure, and the scope of the appended claims is not limited to the following examples.

EXAMPLES

Example 1

Experimental Method 1-1. Luciferase Reporter Assay

NIH3T3 cells were transfected with MSIG, NICD, Tarbp2, Tarbp2 mutants, 4x-RBP-RE-Luc, and renilla luciferase, and then analysis was performed using a luciferase assay kit (Promega).

1-2. Cell Culture

NIH3T3 and 293T cells were cultured in a Dulbecco's modified Eagles medium (DMEM, lonza) treated with 10% fetal bovine serum (FBS, Invitrogen) and 50 ug/ml each of penicillin and streptomycin.

1-3. Virus Infection

HEK293T cells were transfected with a retrovirus vector containing NICD and Tarbp2 genes to prepare virus, and glioma cell culture was infected with the virus.

1-4. RT-PCR

The glioma cells were infected with the virus and cultured for three days. RNA was purified using Ribo-spin (Geneall), and then cDNA was synthesized using an RT-PCR (Takara). Hes1 was examined in this cDNA.

1-5 Immunocytochemistry

The glioma cells infected with the virus were placed on PLO+LM coated plate, and then differentiation was induced using 2% FBS-DMEM media. After 7 days of the differentiation, the glioma cells were fixed by 2% paraformaldehyde. The samples were stained using Tuj1 (early neuronal marker, Covance), Rt-α-GFAP (astrocyte marker, invitrogen), Rb-α-GFP (Green Fluorescent Protein) as a primary antibody, and α-mouse-405, α-rat-555, α-rabbit-488 as a secondary antibody by immunocytochemistry.

1-6. Co-Immunoprecipitation 293T cells were simultaneously transfected with CBF1-HA and Tarbp2-myc and cultured for 48 hours, and lysed at 4° C. for one hour using a lysis buffer (50 mM Tris-HCl [pH 7.5], 150 mM NaCl, 1 mM EDTA [pH 8.0], 0.5% Triton X-100). A sample was prepared such that Mouse-α-myc was treated and remained at 4° C. for 24 hours, 30 ul of protein G sepharose bead was introduced, and centrifuged at 4° C. for 2 hours. The sample was washed three times using a cold lysis buffer, the sample was added with 2x-protein dye, heated for 10 minutes, and then electrophoresed with 12% SDS-PAGE. Western blot was performed using α-HA antibodies.

1-7. Tarbp2 Knock-Down: RNA Interference

In order to prepare shRNA (shTarbp2) (SEQ ID NO. 3) specific to Tarbp2 mRNA, the following oligonucleotide was annealed and ligated to pSIREN vectors fragmented by EcoR1 and BamH1, and then cloning was performed.

(SEQ ID NO. 5)
5'-gatccCCGGCACGTCAGCTACCTGGATATTCTCGAGAATATCCAG
GTAGCTGACGTGTTTTGg-3'

Then, the cloning product was transduced (10% FBS DMEM+polybrene) to glioma cell lines (U373MG) using retrovirus and then was cultured in a $CO_2$ incubator for 2 hours at 37° C.

1-8. Cell Counting shControl (pSIREN vector) and shTarbp2 were introduced into 1×10⁵ glioma cell lines (U373MG) and then cultured in the $CO_2$ incubator for 48 hours at 37° C. Then, cells were dissociated using 0.25% trypsin and then cell counting was performed using a microscope.

1-9. Wound-healing (Migration) Assay shControl (pSIREN vector) and shTarbp2 were introduced into 1×10⁵ glioma cell lines (U373MG), and then cultured in the $CO_2$ incubator for 48 hours at 37° C. Then, cells were put into a 6 well scale plate, and a cell layer was scratched (wound) using a tip one day later. On that day, and one, two, and three days thereafter, it was observed using the microscope that such wound was healed according to migration of cells.

Example 2

Preparation of Recombinant Virus Expressing Tar-RNA Binding Protein2 (Tarbp2)

2-1: Recombinant Virus Vector Preparation

In order to insert a Tarbp2 plasmid to a retrovirus vector, both Tarbp2 vector and retrovirus vector were cut using restriction enzyme Bamh1, and then fragments were mixed and connected by ligase (Takara).

2-2: Retrovirus Preparation (1) Retrovirus Production

HEK 293T cell lines were used as virus packing cell lines. HEK 293T cell lines were co-transfected with the Tarbp2 retrovirus vector prepared in Example 2-1 and two kinds of virus packaging plasmids (VM-GP and VSV-G) using polyethylenimine (PEI) to produce virus.

(2) Retrovirus Collection

Cell culture media of virus production cell lines obtained in the above preparation was collected every 12 hours for 48 hours. Virus collection media was kept at −80° C., this media was gathered together and filtered, and then ultracentrifuged to concentrate the viral particles.

Example 3

Expression of Notch Target Genes 3-1. Retrovirus Infection

The glioma cell lines were infected with the retrovirus produced in Example 2. The glioma cell lines were plated, and cells were infected using polybrene and 10% FBS-DMEM media after a day, cultured at 37° C. for 3 hours, and then the media was exchanged.

3-2. Expression of Notch Target Genes in Protein Levels

The glioma cell lines into which Tarbp2 genes were introduced were lysed to extract proteins, and then the western blotting was performed. Specifically, protein extracts were quantified, protein loading dye and mercaptoethanol were input, heated for 10 minutes, separated by size using SDS-PAGE, and transferred to membranes. These membranes were blocked using 5% skim milk, and then were cultured at 4° C. overnight using rabbit anti Hes1 diluted 1:500 as a primary antibody. Then, the membranes were washed using a TBST buffer, and anti-rabbit-HRP (Horseradish Peroxidase) was treated at room temperature for 2 hours as a secondary antibody.

As a result, as shown in FIG. 1, similar to the glioma cell lines into which the NICD was introduced, in the glioma cell lines into which Tarbp2 genes were introduced, it was observed that protein expression of Hes1 increased compared to green fluorescent proteins (GFPs). In this case, Beta-actin was used as a control group.

3-3. Expression of Notch Target Genes in RNA Levels

The glioma cell lines into which Tarbp2 was introduced were lysed to extract total RNA, and then RT-PCR was performed. Specifically, cDNA was synthesized from the extracted RNA using reverse transcriptase (RTase). Real time-PCR was performed using the synthesized cDNA, and a relative RNA expression level of Hes1, which is a Notch target gene, was identified.

Figure 2:
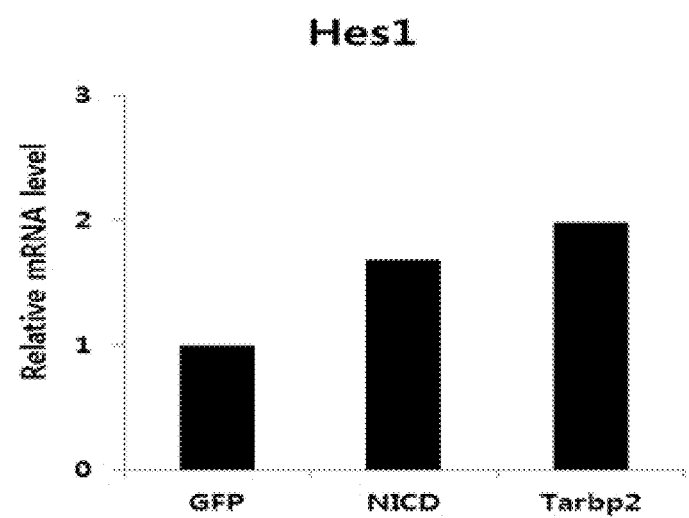
FIG. 2 is a real time PCR result that shows an mRNA transcription amount of Hes1, which is a Notch target gene, when Tarbp2 is transduced in the glioma cell lines. Similar to an NICD group in an activation state of Notch, mRNA transcription of Hes1 increased.

As a result, as shown in FIG. 2, similar to the glioma cell lines into which the NICD was introduced, in the glioma cell lines into which Tarbp2 genes were introduced, it was observed that an RNA expression level of Hes1 increased compared to green fluorescent proteins (GFPs). In this case, Beta-actin was used as a control group.

Example 4

Expression of Notch Target Genes After Knocking Down Tarbp2

Knocking-down retrovirus was prepared using short hairpin RNAs (shhTarbp2) having a sequence complementary to Tarbp2 genes, and then western blotting was performed. Specifically, the glioma cell lines were introduced with the knocking-down retrovirus, and cultured for 36 hours, and then western blotting was performed using the same method as in Example 3-2. A change of a protein expression amount of Notch target genes was identified.

Figure 3:
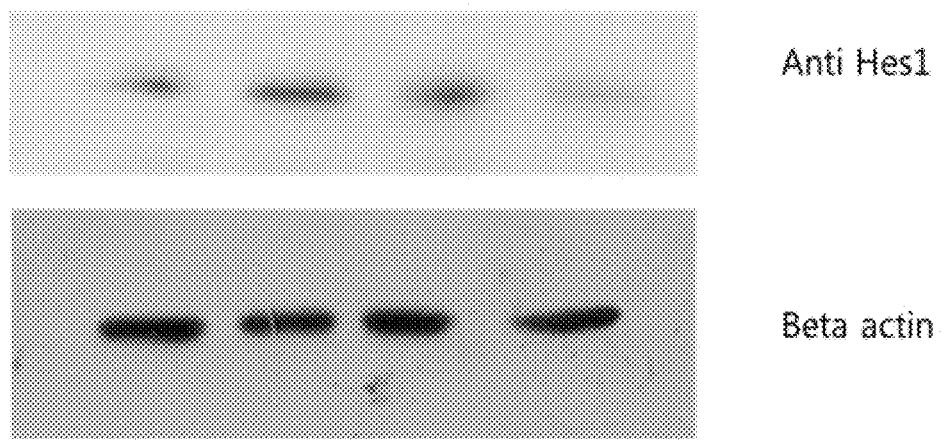
FIG. 3 is a western blot result that shows a change of an expression amount of Hes1, which is a Notch target gene, in glioma cells when expression of Tarbp2 is reduced by introducing short hairpin RNAs having a sequence complementary to Tarbp2 genes (shhTarbp2) into the glioma cell lines. Expression of Hes1 genes decreased.

As a result, as shown in FIG. 3, when expression of Tarbp2 was decreased by introducing short hairpin RNAs having a sequence complementary to Tarbp2 genes into the glioma cell lines, it was identified that protein expression of Hes1, which is a Notch target gene, was inhibited in the glioma cells.

Example 5

Association with Notch Signaling System

The glioma cell lines were infected with Tarbp2 retrovirus and a dominant negative form of MAML1 serving as a co-activator in the Notch signaling system using the same method as in Example 3-1, and cultured. Then, western blotting was performed using the same method as in Example 3-2, and a change of Notch target gene expression in protein levels was identified.

As a result, it was observed that expression of Hes1 decreased in a group in which dominant negative MAML1 (dnMAML1) was treated along with Tarbp2. MAML1 is an important co-activator protein for activating the Notch signaling system. When a function thereof is inhibited, expression of Hes1, which is a Notch target gene, is inhibited, which means that a treated group is associated with Notch complex.

Example 6

Binding of CBF1 and Tarbp2

In order to identify whether Tarbp2 proteins bind to CBF1 binding to promoters of Notch target genes in the Notch signaling pathway, the co-immunoprecipitation method was used. 293T cells were transfected with CBF1-HA and Tarbp2-myc at the same time, cultured for 48 hours, and then the cells were dissolved at 4° C. for 1 hour using a lysis buffer (50 mM Tris-HCl [pH 7.5], 150 mM NaCl, 1 mM EDTA [pH 8.0], and 0.5% TX-100).

Then, a sample was prepared such that Mouse-α-myc was treated, remained at 4° C. for 24 hours, 30 ul of protein G sepharose bead was introduced, and centrifuged at 4° C. for 2 hours. The sample was washed three times using a cold lysis buffer, the sample was added with 2×-protein dye and heated for 10 minutes, and then electrophoresed with 12% SDS-PAGE. Western blot was performed using α-HA antibodies.

As a result, as shown in FIG. 5, it was observed that CBF1 and Tarbp2 were bound to each other, which means that Notch signaling activation of Tarbp2 was performed by binding it to CBF1.

Example 7

Determination of an Effect of Treating Glioma when Tarbp2 Knock-down (RNAi) is Performed 7-1. Inhibition of Glioma Cell Proliferation: Cell Counting shControl (pSIREN vector) and shRNA (shTarbp2) specific to Tarbp2 were introduced into $1 \times 10^5$ glioma cell lines (U373MG), cultured in the $CO_2$ incubator for 48 hours at 37° C. Cells were dissociated using trypsin (0.25%), and cell counting was performed using the microscope.

Figure 6:
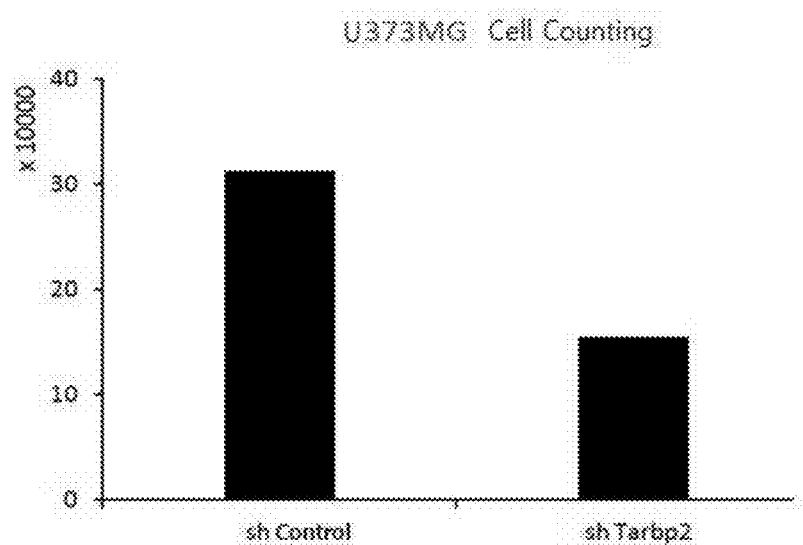
FIG. 6 is a graph showing the result in which shRNA decreasing Tarbp2 expression (shTarbp2) and shControl are introduced into glioma cell lines (U373MG), respectively, and then the number of cells is counted and quantified.

As a result, as shown in FIG. 6, it may be observed that the number of glioma cells was decreased by about 50% in the shTarbp2 group compared to the control group. This means that proliferation of glioma cells can be inhibited when Tarbp2 expression is inhibited.

7-2. Inhibition of Glioma Cell Migration: Wound-healing Assay shControl (pSIREN vector) and shRNA (shTarbp2) (SEQ ID NO. 3) specific to Tarbp2 were introduced into $1 \times 10^5$ glioma cell lines (U373MG), and then cultured in the $CO_2$ incubator for 48 hours at 37° C. Then, cells were put into a 6 well scale plate and a cell layer was scratched (wound) using a tip one day later. On that day, and one, two, and three days thereafter, it was observed using the microscope that such wound was healed according to migration of cells.

Meanwhile, the shTarbp2 hairpin structure is cut by an intracellular mechanisms and results in siTarbp2 having the following sequence (SEQ ID NO. 4: 5'-UGCAGUCGAUG-GACCUAUAA-3')

Figure 7:
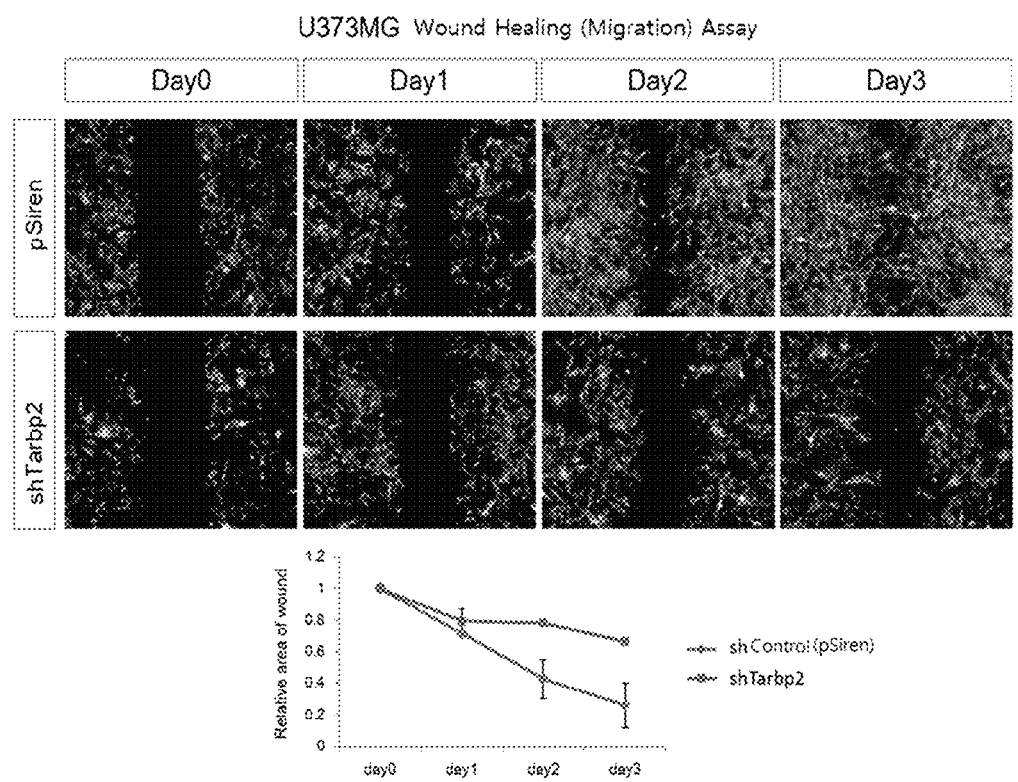
FIG. 7 shows the result in which shRNA decreasing Tarbp2 expression (shTarbp2) and shControl are introduced into glioma cell lines (U373MG), respectively, and then a wound-healing assay capable of identifying U373MG migration is performed.

As a result, as shown in FIG. 7, it may be observed that wound healing according to migration was significantly inhibited in the shTarbp2 group compared to the control group. This means that migration of glioma cells can be inhibited when Tarbp2 expression is inhibited.

Therefore, according to the results, the expression inhibitor of Tarbp2 can be a useful tool capable of treating glioma. In particular, since glioma is cancer having strong permeability and mobility and is easily spread to surrounding tissues, mobility inhibition may be used as an important strategy for treating glioma.

According to the present disclosure, it is possible to provide a new model for research on neural stem cell (NSC) differentiation by discovering a relation between a Notch signaling system and Tarbp2.

According to the present disclosure, it is possible to provide a new target protein for treating glioma.

According to the present disclosure, it is possible to provide a therapeutic agent candidate for glioma.

According to the present disclosure, it is possible to provide a treatment use of glioma as a novel use of Tarbp2.

The above description of the present disclosure is only an example. It may be understood by those skilled in the art that the present invention may be performed in other concrete forms without changing the technological scope and essential features of the present disclosure. Therefore, the above-described examples should be considered as only examples in all aspects and not for purposes of limitation.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Therefore, the scope of the disclosure is defined not by the detailed description, but by the claims and their equivalents, and all variations within the scope of the claims and their equivalents are to be construed as being included in the disclosure.

What is claimed is:

1. A method of treating glioma, comprising administering a Tar RNA binding protein 2 (Tarbp2) expression inhibitor in a pharmaceutically effective amount to a subject in need of glioma treatment,
wherein the expression inhibitor comprises short hairpin RNA (shRNA) consisting of a base sequence of SEQ ID NO. 3 or small interfering RNA (siRNA) consisting of a base sequence of SEQ ID NO. 4 specifically binding to Tarbp2 mRNA, or antisense RNA thereof.

2. The method of claim 1, wherein a gene consisting of a base sequence of SEQ ID NO. 1 encodes the inhibited Tarbp2 protein.

3. The method of claim 1, wherein the inhibited Tarbp2 protein consists of an amino acid sequence of SEQ ID NO. 2.

4. The method of claim 1, wherein the inhibited Tarbp2 binds to C-promoter Binding Factor 1 (CBF1) protein in a Notch signaling pathway.

5. The method of claim 1, wherein the inhibited Tarbp2 increases expression of target gene Hairy and Enhancer of Split-1 (Hes1) in a Notch signaling pathway.

* * * * *

SEQUENCE LISTING

```
<160> NUMBER OF SEQ ID NOS: 5

<210> SEQ ID NO 1
<211> LENGTH: 1038
<212> TYPE: DNA
<213> ORGANISM: Homo Sapiens

<400> SEQUENCE: 1
atgctggccg ccaacccagg caagaccccg atcagccttc tgcaggagta tgggaccaga      60
atagggaaga cgcctgtgta cgaccttctc aaagccgagg gccaagccca ccagcctaat     120
ttcaccttcc gggtcaccgt tggcgacacc agctgcactg gtcagggccc cagcaagaag     180
gcagccaagc acaaggcagc tgaggtggcc ctcaaacacc tcaaaggggg gagcatgctg     240
gagccggccc tggaggacag cagttctttt tctcccctag actcttcact gcctgaggac     300
attccggttt ttactgctgc agcagctgct acccagttc catctgtagt cctaaccagg      360 agcccccca tggaactgca gcccctgtc tccctcagc agtctgagtg caacccgtt         420 ggtgctctgc aggagctggt ggtgcagaaa ggctggcggt gccggagta cacagtgacc      480 caggagtctg ggccagccca ccgcaaagaa ttcaccatga cctgtcgagt ggagcgtttc     540
attgagattg gagtggcac ttccaaaaaa ttggcaaagc ggaatgcggc ggccaaaatg      600
ctgcttcgag tgcacacggt gcctctggat gcccgggatg gcaatgaggt ggagcctgat     660
gatgaccact tctccattgg tgtgggctcc cgcctggatg gtcttcgaaa ccggggccca     720
ggttgcacct gggattctct acgaaattca gtaggagaga agatcctgtc cctccgcagt     780
tgctccctgg gctccctggg tgccctgggc cctgcctgct gccgtgtcct cagtgagctc     840
tctgaggagc aggcctttca cgtcagctac ctggatattg aggagctgag cctgagtgga     900
ctctgccagt gcctggtgga actgtccacc cagccggcca ctgtgtgtca tggctctgca     960
accaccaggg aggcagcccg tggtgaggct gcccgccgtg ccctgcagta cctcaagatc    1020
atggcaggca gcaagtga                                                  1038

<210> SEQ ID NO 2
<211> LENGTH: 345
<212> TYPE: PRT
<213> ORGANISM: Homo Sapiens

<400> SEQUENCE: 2

Met Leu Ala Ala Asn Pro Gly Lys Thr Pro Ile Ser Leu Leu Gln Glu
1               5                   10                  15

Tyr Gly Thr Arg Ile Gly Lys Thr Pro Val Tyr Asp Leu Leu Lys Ala
            20                  25                  30
```

Glu Gly Gln Ala His Gln Pro Asn Phe Thr Phe Arg Val Thr Val Gly
         35                  40                  45

Asp Thr Ser Cys Thr Gly Gln Gly Pro Ser Lys Lys Ala Ala Lys His
 50                  55                  60

Lys Ala Glu Val Ala Leu Lys His Leu Lys Gly Gly Ser Met Leu
 65                  70                  75                  80

Glu Pro Ala Leu Glu Asp Ser Ser Phe Ser Pro Leu Asp Ser Ser
                 85                  90                  95

Leu Pro Glu Asp Ile Pro Val Phe Thr Ala Ala Ala Ala Thr Pro
                100                 105                 110

Val Pro Ser Val Val Leu Thr Arg Ser Pro Pro Met Glu Leu Gln Pro
                115                 120                 125

Pro Val Ser Pro Gln Gln Ser Glu Cys Asn Pro Val Gly Ala Leu Gln
                130                 135                 140

Glu Leu Val Val Gln Lys Gly Trp Arg Leu Pro Glu Tyr Thr Val Thr
145                 150                 155                 160

Gln Glu Ser Gly Pro Ala His Arg Lys Glu Phe Thr Met Thr Cys Arg
                165                 170                 175

Val Glu Arg Phe Ile Glu Ile Gly Ser Gly Thr Ser Lys Lys Leu Ala
                180                 185                 190

Lys Arg Asn Ala Ala Ala Lys Met Leu Leu Arg Val His Thr Val Pro
                195                 200                 205

Leu Asp Ala Arg Asp Gly Asn Glu Val Glu Pro Asp Asp His Phe
                210                 215                 220

Ser Ile Gly Val Gly Ser Arg Leu Asp Gly Leu Arg Asn Arg Gly Pro
225                 230                 235                 240

Gly Cys Thr Trp Asp Ser Leu Arg Asn Ser Val Gly Glu Lys Ile Leu
                245                 250                 255

Ser Leu Arg Ser Cys Ser Leu Gly Ser Leu Gly Ala Leu Gly Pro Ala
                260                 265                 270

Cys Cys Arg Val Leu Ser Glu Leu Ser Glu Glu Gln Ala Phe His Val
                275                 280                 285

Ser Tyr Leu Asp Ile Glu Glu Leu Ser Leu Ser Gly Leu Cys Gln Cys
                290                 295                 300

Leu Val Glu Leu Ser Thr Gln Pro Ala Thr Val Cys His Gly Ser Ala
305                 310                 315                 320

Thr Thr Arg Glu Ala Ala Arg Gly Glu Ala Arg Arg Ala Leu Gln
                325                 330                 335

Tyr Leu Lys Ile Met Ala Gly Ser Lys
                340                 345

<210> SEQ ID NO 3
<211> LENGTH: 58
<212> TYPE: RNA
<213> ORGANISM: Artificial Sequence
<220> FEATURE:
<223> OTHER INFORMATION: Tarbp2 shRNA

<400> SEQUENCE: 3
ccggcacguc agcuaccugg auauucucga gaauaccag guagcugacg uguuuug        58

<210> SEQ ID NO 4
<211> LENGTH: 20
<212> TYPE: RNA
<213> ORGANISM: Artificial Sequence
<220> FEATURE:

```
<223> OTHER INFORMATION: Tarbp2 siRNA

<400> SEQUENCE: 4
ugcagucgau ggaccuauaa                                                20

<210> SEQ ID NO 5
<211> LENGTH: 64
<212> TYPE: DNA
<213> ORGANISM: Artificial Sequence
<220> FEATURE:
<223> OTHER INFORMATION: Tarbp2 oligonucleotide

<400> SEQUENCE: 5
gatccccggc acgtcagcta cctggatatt ctcgagaata tccaggtagc tgacgtgttt    60
ttgg                                                                 64
```